United States Patent [19]

Stephenson

[11] 4,102,753

[45] Jul. 25, 1978

[54] DISTILLATION OF META-CHLORONITROBENZENE IN THE PRESENCE OF A DISTILLATION ADJUVANT

[75] Inventor: Richard M. Stephenson, Storrs, Conn.

[73] Assignee: PPG Industries, Inc., Pittsburgh, Pa.

[21] Appl. No.: 836,256

[22] Filed: Sep. 23, 1977

[51] Int. Cl.$^2$ .......................... B01D 3/34; B01D 3/36
[52] U.S. Cl. ...................................... 203/64; 260/646
[58] Field of Search ........................... 203/64; 260/646

[56] References Cited

U.S. PATENT DOCUMENTS 3,368,365  2/1968  Dunn .................................. 203/48 X

*Primary Examiner*—Leland A. Sebastian
*Attorney, Agent, or Firm*—Irwin M. Stein

[57] ABSTRACT

This invention relates to the azeotropic distillation of a mixture of meta-chloronitrobenzene isomers employing a lower alkylene glycol, lower oxyalkylene glycol or glycerol as the entrainer or azeotrope former. The invention has several distinct advantages, not the least of which that significantly lower still bottom temperatures can be employed, thus reducing the problems associated with the decomposition and potential explosive decomposition of nitroaromatic compounds. In addition improvements in the relative volatility of meta-chloronitrobenzene, as compared to its isomers have been accomplished.

14 Claims, No Drawings

DISTILLATION OF META-CHLORONITROBENZENE IN THE PRESENCE OF A DISTILLATION ADJUVANT

BACKGROUND OF THE INVENTION

The compound meta-chloroanaline, which is a desired herbicide intermediate, has most usually been prepared from meta-chloronitrobenzene.

One method used to form meta-chloronitrobenzene involves the chlorination of nitrobenzene. The resultant product is primarily meta-chloronitrobenzene, but in combination with significant amounts of both its para- and ortho- isomers.

The separation of chloronitrobenzene isomers is inherently extremely difficult by the use of simple distillation, the boiling points of meta-, para- and ortho- chloronitrobenzenes being respectively 234° C., 238.5° C and 245.5° C. At least where the further product of relatively pure metachloroanaline is contemplated, one can not look to postpone complete isomer separation until after the reduction step, since both metachloroanaline and parachloroanaline boil at 231° C. with ortho-chloroanaline boiling at 208.4° C.

While distillation of chloronitrobenzene isomers can yield some significant separation, if a column having a large number of theoretical plates is employed, care must be taken in employing a still temperature which is too high, for example approaching 300° C., since decomposition, and even explosive decomposition of the chloronitrobenzene can be expected.

Among the known chloronitrobenzene isomer separation processes are the following:

U.S. Pat. No. 3,311,666, to Dunn, relates to the separation of chloronitrobenzene isomers by crystallization and fractionation and describes the difficulties encountered in distillation and crystallization techniques.

U.S. Pat. No. 3,816,551, to Lee, relates to the use of crystallization in separating isomers of chloronitrobenzene. Specifically, the para isomer is separated employing continuous crystallization in the presence of water.

U.S. Pat. Nos. 2,795,620 and 2,795,621, to Bloom et al, discuss various known methods for the manufacture of metachloronitrobenzene and problems relating to chloronitrobenzene isomer separation. The patents are specifically directed to separating ortho- and para- chloronitrobenzenes from metachloronitrobenzene by means of a sulfonation process.

U.S. Pat. No. 2,245,945, to van Dejck et al, relates to a process for the separation of isomeric organic compounds, including mixture of ortho- and para-chloronitrobenzene, by the use of two selective immiscible solvents to cause distribution of the isomers between the solvents.

U.S. Pat. No. 3,051,650, to Pfennig, relates to separating chemical compounds using solvents and liquified sulfur dioxide.

While a number of compounds, including some of the compounds employed in the process of the invention have been individually known to form binary azeotropes with at least one chloronitrobenzene isomer, the state of the distillation art is not sufficiently advanced so that one can readily predict that because a compound forms a binary azeotrope, that the same compound will be useful in a ternary or quaternary system, or that because one compound is effective, that another apparently closely structurally related compound will be effective. Therefore, most azeotropes are chance discoveries.

The following binary systems have been reported in "Azeotropic Data" No. 6 of the Advance in Chemistry Series. American Chemical Society, Washington D. C. (1952), at the indicated page number:

m-chloronitrobenzene/dipropylene glycol, b.p. <227.0° C (page 157);

o-chloronitrobenzene/triethylene glycol, no azeotrope (page 157);

ethylene glycol/m-chloronitrobenzene, b.p. 192.5° C, 53% glycol (page 64);

ethylene glycol/o-chloronitrobenzene, b.p. 193.5° C, 68% glycol (page 64);

ethylene glycol/p-chloronitrobenzene, b.p. 192.85° C, 57.8% glycol (page 64);

propylene glycol azeotropes with unrelated compounds (page 101).

Maurice Lecat, *Am. Soc. Sci. Bruxelles, Ser. I, Vol.* 61, pages 79–98 (1947) reports the following binary azeotropes systems:

ethylene glycol/m-chloronitrobenzene b.p. 192.5° C (page 84);

glycerol/m-chloronitrobenzene, b.p. 232.2° C (page 84);

dipropylene glycol/m-chloronitrobenzene, b.p. <227.0° C (page 86);

dipropylene glycol/p-chloronitrobenzene, b.p. <228.3° C (page 86);

trimethylene glycol/p-chloronitrobenzene, b.p. <234.0° C (page 86);

diethylene glycol/m-chloronitrobenzene, b.p. 228.2° C (page 86);

diethylene glycol/p-chloronitrobenzene, b.p. 229.5° C (page 86);

diethylene glycol/o-chloronitrobenzene, b.p. 233.5° C (page 86).

As can be seen from the above data many of the individual chloronitrobenzene isomer binary azeotropes with a particular polyol have boiling points closer to each other, than do the isomers per se. If anything, this would appear to suggest away from the use of ternary or quaternary azeotropes as disclosed below.

DESCRIPTION OF THE INVENTION

This invention relates to the distillation of a mixture of chloronitrobenzene isomers, principally containing meta-chloronitrobenzene, in the presence of a distillation adjuvant which forms an azeotrope with, or entrains metachloronitrobenzene, providing at least a lower still pot temperature for the distillation of meta-chloronitrobenzene, while preferably enriching the amount of the meta isomer in the distillation column overhead, in comparison with the amount of at least one of para-chloronitrobenzene or ortho-chloronitrobenzene as contained in the mixture being distilled.

In a preferred embodiment the distillation adjuvant phase separates from the distillate, which aids in the separation of the distillation adjuvant from the chloronitrobenzene distillate.

The chloronitrobenzene isomer mixtures which can be distilled, and preferably enriched by the process of this invention, include chloronitrobenzene isomer mixtures containing at least a majority of meta-chloronitrobenzene in admixture with at least one, and usually both the ortho- and para- isomers. Preferably, the mixture contains at least about 60%, preferably at least 70%, and most preferably at least about 80% of the meta isomer.

The distillation adjuvants employed in the process of this invention are selected from glycerol or lower alkylene glyols or their dimers i.e. lower oxyalkylene glyols having eight, and preferably six carbon atoms or less. Among the presently preferred adjuvants are ethylene glycol; dipropylene glycol; 1,4-butanediol; 2,5-hexanediol; propylene glycol; glycerol; and diethylene glycol. The most preferred adjuvants are ethylene glycol and propylene glycol, with propylene glycol being especially preferred. Both ethylene glycol and propylene glycol at least partially phase separate from the chloronitrobenzene distillate when cooled to a temperature near ambient temperature.

In the process of the invention, a mixture of the chloronitrobenzene isomers and the distillation adjuvant are distilled through a distillation apparatus, for example, a distillation column having at least one and preferably a multiplicity of theoretical plates of separation.

Preferably the distillation process of the ivention is conducted at a reflux ratio (L/D) of between about 1:1 and about 20:1. Typically, a reflux ratio of about 10:1 is employed.

The amount of the distillation adjuvant admixed with the chloronitrobenzene isomer mixture can vary considerably. Usually, the ratio of adjuvant to isomer mixture is between about 0.1:1 to about 8:1. When propylene glycol or ethylene glycol are employed a ratio of about 0.5:1 to about 8:1 is preferred, with a ratio of about 4:1 being considered optimum.

Generally, the amount of the distillation adjuvant employed is that amount which, when admixed with the chloronitrobenzene isomer mixture to be distilled, provides a metachloronitrobenzene containing distillate having a boiling point lower than the boiling point of meta-chloronitrobenzene. Most preferably the distillation adjuvant is selected to and employed in an amount which provides a meta-chloronitrobenzene distillate which not only has a boiling point lower than metachloronitrobenzene, but which also contains a higher ratio of metachloronitrobenzene to ortho- and/or para-chloronitrobenzene than the ratio of meta-chloronitrobenzene to ortho- and/or para-chloronitrobenzene in the isomer mixture being distilled.

In the distillation process, at least a portion of the distillation adjuvant is distilled with the meta-chloronitrobenzene. The resultant mixture, comprising meta-chloronitrobenzene and distillation adjuvant, can be worked up to remove the adjuvant or alternatively the mixture may be employed in a chemical conversion of the meta-chloronitrobenzene, for example, the reduction of meta-chloronitrobenzene to meta-chloroanaline and the distillation adjuvant then removed, if desired.

Where appropriate, the chloronitroaromatic component can be at least partially separated from the distillation adjuvant in a phase separator maintained at a temperature, below the distillation temperature, at which phase separation occurs. If desired the separated distillation adjuvant can then be recycled to the distillation process.

As there is a substantial difference in solubility between the aromatic component and the distillation adjuvant, the adjuvant can be removed from the aromatic component by washing the mixture of aromatic component and distillation adjuvant with water or another appropriate solvent in which the distillation adjuvant is selectively soluble. Such a separation step is a step well within the skill of the art.

There follow several examples setting forth embodiments of the invention. It should be understood that these examples are illustrative rather than limiting. Unless otherwise specified, in the examples and throughout the specification all parts and percentages are by weight, and all temperatures are degrees Centigrade.

In the examples relative volatilities and related parameters are expressed as follows:

$$\alpha_{a-b} = \frac{Y_a/Y_b}{X_a/X_b}$$

where $\alpha_{a-b}$ = relative volatility of a compared to b;
$Y_a$ = vaoor composition of a (mole %)
$Y_b$ = vapor composition of b (mole %)
$X_a$ = liquid composition of a (mole %)
$X_b$ = liquid composition of b (mole %)

EXAMPLE 1

A number of compounds were screened as possible azeotropic agents in an apparatus consisting of a 250 ml., 3 necked Pyrex flask equipoed with a heating mantle, condenser and an ASTM or a Beckman thermometer. Initially, 25 ml. of a lower boiling material was charged into the point and the system was brought to boiling. Temperature readings were taken every two minutes at the boiling point until the temperature discrepency was less than 0.1° C. Once the constant temperature criteria was satisfied, approximately ½ ml. of a higher boiling component was added through the condenser and the change in temperature was noted. A drop in temperature was an indication of a minimum boiling azeotrope formation, therefor the procedure of adding ½ ml. of higher boiling component was continued until the boiling point began to rise again.

Table 1.

| Azeotrope Formation With Chloronitrobenzenes | | |
|---|---|---|
| | MCNB | PCNB |
| o-cresol | no | no |
| m-cresol | no | no |
| p-cresol | no | no |
| 2-methyl-2,4-pentanediol | no | no |
| n-octyl alcohol | no | no |
| trichloroacetic acid | no | no |
| o-toluidine | no | no |
| m-toluidine | no | no |
| p-toluidine | no | no |
| N,N-dimethylaniline | no | no |
| 3-aminopropanol | reacts | reacts |
| 1,2-propanediol | yes | yes |
| 1,3-propanediol | no | no |
| isophorone | no | no |
| veratrole | no | no |
| 3,4-dichlorotoluene | no | no |
| benzyl alcohol | no | no |
| 1,3-butanediol | no | no |
| 1,4-butanediol | yes | yes |
| 1,2,4-trichlorobenzene | no | no |
| 2-ethylhexanoic acid | no | no |
| dipropylene glycol | yes | yes |
| 2,6-dimethylphenol | no | no |
| 3,5-dimethylphenol | no | no |
| 2,3-dimethylphenol | no | no |
| 2,5-dimethylphenol | no | no |
| 3,4-dimethylphenol | no | no |
| 2,5-hexanediol | yes | yes |
| ethylene glycol | yes | yes |
| o-anisidine | no | no |
| benzyl acetate | no | no |
| benzyl formate | no | no |
| 2,4-dichlorophenol | no | no |
| p-dimethoxybenzene | no | no |
| 3,4-dimethylaniline | no | no |
| 2,4-dimethylaniline | no | no |
| N-ethylaniline | no | no |

91% MCNB products were isolated from the atmospheric distillation and 93% MCNB products from the azeotropic distillation.

The composition of the azeotrope with propylene glycol was analyzed and showed 3-10% of the azeotrope separated as the CNB phase at 55° C.

For comparison purposes, a synthetic mixture of CNB isomers was distilled using a simple 1-plate distillation. The still consisted of a 16 inch × 0.75 inch Vigeraux column which was wrapped with a heating tape and asbestos cloth for column heat, a 500-ml, 4-necked flask, and an automatic head from a Todd still. Heat was supplied to the pot by means of an electric heating mantle. For the azeotropic distillations a micro-Dean-Stark head was employed. Hot water (~80° C) was circulated through the condensers to keep the product from freezing. The synthetic CNB isomer mixture consisted of 80% MCNB, 15% OCNB and 5% PCNB. The atmospheric distillation was run at 20:1 reflux ratio and the first 4% of product was taken as two, 2% fractions and analyzed. The azeotropic distillations were first run employing the regular refluxing Todd still head, but the CNB isomers were fairly soluble in the glycols (at 55° C a mixture of 3 ml of mixed CNB isomers and 10 ml of propylene glycol separated only 0.3 ml of a CNB phase, at room temperature the CNB phase increased to 0.8 ml). A micro-Dean-Stark head of 2 ml capacity was then employed for the azeotropic distillation and the first 5% of CNB isomers which separated (lower phase) was taken for analysis. The product was kept warm and molten by the heat from a heat lamp. Details of the distillations and results are set forth in Table 5.

The results in Table 5 indicate an improved separation compared to atmospheric distillations, can be achieved using either ethylene or propylene glycol as entrainer in an azeotropic distillation. Some glycol remained in the purified product, but this could be readily washed out after the catalytic reduction of the CNB isomers to chloroanilines.

The last two experiments noted in Table 5 were carried out to show that the purification of the CNB isomer was not the result of the preferential extraction of undesired isomers into the glycol. It can be seen that little or no enrichment of the MCNB content occur by simply contacting the CNB isomers with glycol and it was concluded that it is the azeotropic distillation which accomplishes the purification.

In Table 6 the results of distillation of a real feed derived from the chlorination of nitrobenzene is reported. In these distillations a multiplate, glass Widmer column was used. The plate valve was estimated as 15. The results in Table 6 again show the enhancement obtained by using propylene glycol as an entrainer. In Table 6 the results have also been calculated to show the composition of the CNB isomers in the product. These "corrected" values assumed that it would be relatively easy to isolate the CNB isomers, from the low and high boilers brought over with the propylene glycol, by means of a simple polishing still and/or washing of the product. A significant portion of the lights in the azeotropic distillation appear to be derived from propylene glycol impurities and are probably water soluble and the dichloronitrobenzenes are so high boiling that the CNB isomers are readily separated in a simple distillation.

TABLE 5

| | Distillation of CNB Isomers Through 1-Plate Vigreaux Column | | | | | | |
|---|---|---|---|---|---|---|---|
| | | Peak Area % in Product[1] | | | | | |
| Distillation | Temp. ° C | PCNB | MCNB | OCNB | Glycol | α MCNB–PCNB | α MCNB–OCNB |
| Feed | — | 4.4 | 80.9 | 14.9 | — | | |
| Atmospheric 1:1 CNB: | 232–234 | 4.4 | 85.0 | 10.7 | — | 1.11 | 1.51 |
| Propylene glycol | 184 | 3.8 | 87.7 | 8.5 | 5.3 (55° C) | | |
| | | 3.9 | 87.3 | 8.8 | 1.1 (RT) | 1.22 | 1.81 |
| 1:4 CNB: Propylene glycol | 185 | 3.4 | 88.8 | 7.7 | 1.0 (RT) | 1.42 | 2.10 |
| 1:4 CNB: Ethylene glycol | 190 | 3.7 | 88.6 | 7.8 | — | 1.30 | 2.06 |
| CNB Phase From Mixing 1 CNB with 4 Propylene glycol | — | 4.6 | 81.1 | 14.4 | 8.9 (55° C) | | |
| | | 4.3 | 82.2 | 13.5 | 1.1 (RT) | 0.96 | 1.02 |
| CNB Phase from Mixing 1 CNB with 4 Ethylene glycol at 55° C | — | 5.8 | 81.5 | 12.7 | — | 1.01 | 1.24 |

[1]Percent PCNB, MCNB and OCNB calculated ignoring the glycol content.

TABLE 6

| | | | | Distillation in Widmer Column[1] | | | | | | |
|---|---|---|---|---|---|---|---|---|---|---|
| | | | | Peak Area % | | | | | Peak Area % (Corrected)[3] | |
| Fraction | Head Temp. ° C | % of Feed | Σ % of Feed | Lights[5] | PCNB | MCNB | OCNB | High Boiling[6] | PCNB | MCNB | OCNB |
| | | | | Atmospheric Distillation[2] | | | | | | | |
| Feed[4] | — | 100 | 100 | 0.2 | 4.3 | 75.2 | 13.7 | 6.5 | 4.6 | 80.7 | 14.7 |
| 1 | 229 | 0.9 | 0.9 | 1.2 | 3.8 | 90.7 | 4.1 | 0.2 | 3.9 | 92.0 | |
| 2 | 232 | 0.9 | 1.8 | 0.9 | 4.0 | 91.1 | 3.9 | 0.2 | 4.0 | 92.0 | 3.9 |
| 3 | 232 | 1.4 | 3.2 | 0.7 | 4.0 | 91.1 | 4.0 | 0.2 | 4.0 | 92.0 | 3.9 |
| 4 | 232 | 1.4 | 4.6 | 0.7 | 3.9 | 90.7 | 4.7 | 0.1 | 3.9 | 91.3 | 4.7 |
| 5 | 232.5 | 1.8 | 6.4 | 0.5 | 4.1 | 91.1 | 4.2 | 0.2 | 4.1 | 91.6 | 4.2 |
| 6 | 232.5 | 2.3 | 8.7 | 0.4 | 3.7 | 91.9 | 3.9 | 0.2 | 3.7 | 91.4 | 3.9 |
| | | | | Azeotropic Distillation - 1 CNB: 4 Propylene glycol | | | | | | | |
| Feed[4] | — | 100 | 100 | 0.2 | 4.3 | 75.2 | 13.7 | 6.5 | 4.6 | 80.7 | 14.7 |
| 1 | 179–181 | 2 | 2 | 11.4 | 2.5 | 83.5 | 1.6 | 1.1 | 2.9 | 95.3 | 1.8 |
| 2 | 181–182 | 2 | 4 | 2.6 | 2.9 | 92.5 | 1.3 | 0.8 | 3.0 | 95.7 | 1.3 |
| 3 | 177–182 | 2 | 6 | 3.0 | 2.9 | 91.3 | 1.9 | 1.0 | 3.0 | 95.0 | 2.0 |
| 4 | 177–182 | 2 | 8 | 2.1 | 2.7 | 92.5 | 1.2 | 1.5 | 2.8 | 95.9 | 1.2 |
| 5 | 177–182 | 2 | 10 | 1.3 | 2.7 | 92.3 | 1.9 | 1.8 | 2.8 | 95.3 | 1.9 |

Table 1.-continued

Azeotrope Formation With Chloronitrobenzenes

|  | MCNB | PCNB |
|---|---|---|
| o-ethylaniline | no | no |
| p-ethylphenol | no | no |
| heptanoic acid | yes | yes |
| hexanoic acid | no | no |
| methyl salicylate | no | no |
| o-nitrophenol | dec | dec |
| o-nitrotoluene | no | no |
| propiophenone | no | no |
| triethyl phosphate | no | no |
| acetamide | yes | yes |
| triethylbenzene | no | no |
| m-nitrotoluene | yes | no |
| p-nitrotoluene | yes | yes |
| naphthalene | no | no |
| dimethyl benzylamine | no | no |
| valeric acid | no | no |
| o-tert butyl phenol | no | no |
| tetrahydrofurfuryl alcohol | no | no |
| 2-octanol | no | no |
| 2-ethyl-1-hexanol | no | no |
| isovaleric acid | no | no |
| ethanolamine | no | no |
| furfural | no | no |
| butyric acid | no | no |
| maleic anhydride | no | no |
| acetophenone | no | no |
| propiophenone | no | no |
| 1,3-dimethyl-2-nitrobenzene | no | no |
| formamide | no | no |
| N-methylaniline | no | no |
| diethylene triamine | no | no |
| ethyl benzoate | no | no |
| N,-N-diethylaniline | no | no |
| N,N-diethyl-m-toluidine | no | no |
| methyl benzoate | no | no |
| phenethyl alcohol | no | no |
| α-methyl benzyl alcohol | no | no |
| benzonitrile | no | no |
| benzyl amine | no | no |
| tributyl amine | no | no |
| aniline | no | no |
| diethyl succinate | no | no |
| tetrahydronaphthalene | no | no |
| 2(2-ethoxy ethoxy) ethanol | no | no |
| p-chlorophenol | no | no |
| 2,2-dimethyl-1,3-propanediol | no | no |
| 1,6-hexanediamine | no | no |
| methyl p-toluate | no | no |
| ethyl salicylate | no | no |

EXAMPLE 2

1,2-propane diol (propylene glycol); 1,4-butanediol, 2,5-hexanediol; dipropylene glycol; ethylene glycol and glycerol were tested in a 1½ by 30 inches still packed with 24 inches of 3/32 inch glass helices for their utility for recovering meta-chloronitrobenzene from a meta-para mixture. Initially, a small amount of meta-para mixture was added into the columns and the system was brought to boiling under total reflux. Once a steady state was reached a small amount of known entrainer was added and the system was allowed to equilibrate. The overhead samples taken before and after the addition of an entrainer were analyzed for meta and para content. The procedures of addition of a known amount of entrainer was continued until an optimum entrainer to organic ratio was obtained. The results indicate that propylene glycol is the most promising entrainer (Table 2). When a mixture containing 56% meta-/44% para-chloronitrobenzene was put through the still with a 4:1 ratio of propylene glycol to organic, a 75.7% meta-/24.3% para composition was obtained in the overhead at 185° C. and atmospheric pressure. The same feed material produced a 63.6% meta/36.4% para composition in the overhead in the absence of propylene glycol. Overhead compositions at various other propylene glycol to isomer ratios with the same feed material are summarized in Table 3.

Table 2

| Entrainer | Wt. Ratio Entrainer/Aromatics | | | |
|---|---|---|---|---|
|  | 0.2:1 | 0.5:1 | 1:1 | 2:1 |
| ethylene glycol | 63.9% MCNB | 64.1% MCNB | 65.2% MCNB | 66.6 MCNB |
| dipropylene glycol | 61.9 | 63.1 | 63.2 | — |
| 1,4-butanediol | 65.8 | 65.3 | 64.7 | 64.3 |
| 2,5-hexanediol | 68.1 | 63.3 | 63.3 | 64.5 |
| propylene glycol | 63.8 | 64.5 | 66.7 | 69.4 |
| glycerol | 61.0 | 60.6 | 60.5 | 60.2 |
| diethyleneglycol | 61.9 | 63.1 | 62.1 | 63.5 |

Table 3

| Wt. Ratio Entrainer/ Isomer Mixtures | % meta-chloronitro-benzene Using Ethylene Glycol | % metal-chloro-nitrobenzene using Propylene Glycol |
|---|---|---|
| 1:1 | 68.6% | 66.9% |
| 2:1 | 70.2 | 71.8 |
| 3:1 | 70.9 | 72.8 |
| 4:1 | 68.6 | 75.7 |
| 6:1 | 67.5 | 70.2 |
| 8:1 | 67.4 | 71.2 |

It was also noted that propylene glycols phase separated from the cloronitrobenzenes in the receiver and did not display much mutual solubility. Ethylene glycol also phase separated.

Table 4.

| Summary of Vapor-Liquid Equilibrium Data | | | |
|---|---|---|---|
| Propylene Glycol: Wt. Ratio PG | $X_a$ | $Y_b$ | α (MCNB-PCNB) |
| 1:1 | 0.494 | 0.517 | 1.099 |
| 1.5:1 | 0.499 | 0.521 | 1.09 |
| 2:1 | 0.488 | 0.513 | 1.112 |
| 2.5:1 | 0.490 | 0.522 | 1.137 |
| 3:1 | 0.500 | 0.528 | 1.12 |
| 3:1 | 0.494 | 0.519 | 1.11 |
| 3.5:1 | 0.483 | 0.5175 | 1.147 |
| 4:1 | 0.491 | 0.518 | 1.11 |
| 4.5:1 | 0.799 | 0.8235 | 1.175 |
| 6:1 | 0.475 | 0.502 | 1.113 |
| 11.1 | 0.476 | 0.496 | 1.08 |
| Ethylene Glycol: Wt. Ratio EG | $X_a$ | $Y_b$ | α (MCNB-PCNB) |
| 1:1 | 0.485 | 0.513 | 1.116 |
| 2:1 | 0.482 | 0.513 | 1.137 |
| 6:1 | 0.466 | 0.508 | 1.185 |
| 12.1 | 0.468 | 0.509 | 1.185 |

EXAMPLE 3

Comparison of the products of CNB isomer mixtures separated by azeotropic and regular atmospheric distillation in 1-plate and 15-plate glass columns indicated that the azeotropic distillations with ethylene or propylene glycol offered an improved means of separation (products contained higher concentrations of the meta isomer). In the 1-plate distillation products containing 85% MCNB were isolated from feed containing 5% PCNB, 80% MCNB, and 15% OCNR by atmospheric distillation while azeotropic distillation with 1:4 CNB: glycol yielded products containing 89% MCNB using either ethylene or propylene glycols as entrainer. In the 15-plate distillation the feed contained 75% MCNB and TABLE 6-continued

| Fraction | Head Temp. °C | % of Feed | Σ % of Feed | Distillation in Widmer Column[1] | | | | | Peak Area % (Corrected)[3] | | |
|---|---|---|---|---|---|---|---|---|---|---|---|
| | | | | Peak Area % | | | | High Boiling[6] | | | |
| | | | | Lights[5] | PCNB | MCNB | OCNB | | PCNB | MCNB | OCNB |
| 6 | 177-182 | 2 | 12 | 0.8 | 3.0 | 93.9 | 1.6 | 1.6 | 3.0 | 94.9 | 1.6 |
| 7 | 177-182 | 3 | 15 | 0.9 | 3.0 | 93.5 | 1.7 | 1.7 | 2.9 | 95.2 | 1.7 |

[1]20.3 cm Column, Cat. No. 6581, ACE Glass Inc. Catalog 700,1977, ~ 15 plates.
[2]740 mm
[3]Assuming only PCNB, MCNB and OCNB present.
[4]CNB isomer mixture isolated from chlorination of nitrobenzene (468-316), contained traces of nitrobenzene and dichloronitrobenzenes.
[5]Mainly nitrobenzene in the atmospheric distillation and nitrobenzene and one impurity from the propylene glycol in the azeotropic distillation.
[6]Mainly 2,5-dichloronitrobenzene in both distillations. The feed also contained a little 3,4-dichloronitrobezene but none was detected in the distillates.

The analysis of the CNB isomer was made using a Model A-90-P Aerograph gas chromatograph. Separation of the isomers was accomplished by injecting one microliter of sample (more caused the peaks to coalesce) into a 12 ft by ⅛ in. stainless steel column of 15% Seponate DS-10 on Chromosorb W 100/120 with the injection port (glass lined) at 180° C and the column held isothermally at 200° C (gas flow was 25 cc/min, the detector temperature 230° C and filament current 225 μA). Several injections of mixed CNB isomers were made at the beginning of each day to saturate the column. At least 2 analyses of each sample was made and the results averaged. The results were calculated as peak area percents from the areas as found by manual triangulation.

TABLE 7

| Entrainer | | Vapor-Liquid Equilibrium Data for Typical Feed | | | | | | | |
|---|---|---|---|---|---|---|---|---|---|
| | | Liquid | | | Vapor | | | αMCNB | αMCNB |
| | | MCNB | PCNB | OCNB | MCNB | PCNB | OCNB | PCNB | OCNB |
| none | | 75.8% | 6.21% | 18.05% | 80.0% | 6.0% | 14.0% | 1.09 | 1.36 |
| propylene glycol | 1:1 | 76.5 | 5.4 | 18.1 | 80.1 | 5.7 | 14.2 | 1.045 | 1.35 |
| propylene glycol | 4:1 | 76.8 | 5.8 | 17.4 | 80.5 | 5.7 | 13.8 | 1.06 | 1.32 |
| propylene glycol | 6:1 | 77.4 | 5.6 | 17.0 | 81.65 | 5.45 | 12.9 | 1.09 | 1.39 |
| Propylene glycol | 20:1 | 77.6 | 6.1 | 16.3 | 82.1 | 5.95 | 11.95 | 1.085 | 1.44 |
| ethylene glycol | 1:1 | 75.0 | 6.05 | 18.9 | 79.8 | 6.35 | 13.9 | 1.01 | 1.44 |
| ethylene glycol | 2:1 | 75.75 | 6.25 | 18.0 | 81.1 | 5.9 | 13.0 | 1.13 | 1.48 |
| ethylene glycol | 4:1 | 75.3 | 6.3 | 18.4 | 81.3 | 5.9 | 12.8 | 1.14 | 1.55 |
| ethylene glycol | 10:1 | 74.4 | 6.3 | 19.3 | 80.9 | 5.9 | 13.2 | 1.16 | 1.58 |
| ethylene glycol | 20:1 | 73.8 | 6.4 | 19.8 | 79.5 | 5.85 | 14.7 | 1.17 | 1.45 |

While specific examples of the invention have been set forth hereinabove the invention is not limited thereto, but includes all the variations and modifications as disclosed above and set forth in the appended claims. For example, other isomer mixtures and adjuvants in varying proportions, as set forth above, can be employed in place of those exemplified. It is noted that while the process has been described as being conducted at atmospheric pressure, the process can be conducted at pressure both above and below atmospheric pressure, if desired.

What is claimed is:
1. A distillation method comprising:
   (a) distilling a mixture comprising
      (i) a mixture of chloronitrobenzene isomers containing a majority of meta-chloronitrobenzene in admixture with at least one of its isomers and
      (ii) a distillation adjuvant selected from the group consisting of lower alkylene glycols, lower oxyalkylene glycols or glycerol
   said distillation adjuvant being present in an amount which provides a meta-chloronitrobenzene distillate having a boiling point lower than the boiling point of meta-chloronitrobenzene, and
   (b) recovering a distillate comprising meta-chloronitrobenzene.
2. The method, as in claim 1, where the distillation adjuvant is present in an amount which provides a meta-chloronitrobenzene containing distillate which contains a higher ratio of meta-chloronitrobenzene than the ratio of meta-chloronitrobenzene in the isomer mixture being distilled.
3. The method, as in claim 1, where the ratio of (ii) to (i) is about 0.1 to about 8:1.
4. The method, as in claim 3, where the ratio of (ii) to (i) is about 0.5:1 to about 8:1.
5. The method, as in claim 1, where the distillation adjuvant is selected from the group consisting of ethylene glycol; dipropylene glycol; 1,4-butanediol; 2,5-hexanediol; propylene glycol; glycerol and diethylene glycol.
6. The method, as in claim 5, where the distillation adjuvant is present in an amount which provides a meta-chloronitrobenzene containing distillate which contains a higher ratio of meta-chloronitrobenzene than that ratio of meta-chloronitrobenzene in the isomer mixture being distilled.
7. The method, as in claim 5, where the ratio of (ii) to (i) is about 0.1 to about 8:1.
8. The method, as in claim 7, where the ratio of (ii) to (i) is about 0.5:1 to about 8:1.
9. The method, as in claim 1, where the distillation adjuvant is propylene glycol.
10. The method, as in claim 9, where the distillation adjuvant is present in an amount which provides a meta-chloronitrobenzene containing distillate which contains a higher ratio of meta-chloronitrobenzene than the ratio of meta-chloronitrobenzene in the isomer mixture being distilled.
11. The method, as in claim 9, where the ratio of (ii) to (i) is about 0.1 to about 8:1.
12. The method, as in claim 9, where the ratio of (ii) to (i) is about 0.5:1 to about 8:1.
13. The method, as in claim 9, where the distillation is conducted at a reflux ratio between about 1:1 to about 1:20.
14. The method, as in claim 9, comprising the additional steps of
   (c) cooling the recovered distillate comprising meta-chloronitrobenzene and propylene glycol sufficiently to form two phases comprising a meta-chloronitrobenzene rich phase and a propylene glycol rich phase and
   (d) recycling the propylene glycol distillation adjuvant.

* * * * *